United States Patent
Masada et al.

(10) Patent No.: US 7,827,982 B2
(45) Date of Patent: Nov. 9, 2010

(54) EJECTION LIQUID AND EJECTION METHOD

(75) Inventors: Yohei Masada, Tokyo (JP); Masaru Sugita, Tokyo (JP); Hideki Kaneko, Yokohama (JP); Takeshi Miyazaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 908 days.

(21) Appl. No.: 11/724,299

(22) Filed: Mar. 15, 2007

(65) Prior Publication Data

US 2008/0029083 A1 Feb. 7, 2008

Related U.S. Application Data

(63) Continuation-in-part of application No. 11/570,744, filed as application No. PCT/JP2005/018247 on Sep. 27, 2005.

(30) Foreign Application Priority Data

| Sep. 27, 2004 | (JP) | ............................. 2004-279864 |
| Aug. 31, 2005 | (JP) | ............................. 2005-252154 |
| Mar. 27, 2006 | (JP) | ............................. 2006-085565 |

(51) Int. Cl.
  *A61M 11/00* (2006.01)
(52) U.S. Cl. ............................. 128/200.14; 128/200.16; 514/3
(58) Field of Classification Search ............ 128/200.14, 128/200.16; 514/3, 557, 866
See application file for complete search history.

(56) References Cited

U.S. PATENT DOCUMENTS

| 5,894,841 | A | 4/1999 | Voges .................... 128/203.12 |
| 6,120,761 | A | 9/2000 | Yamazaki et al. .......... 424/85.1 |
| 6,277,367 | B1 | 8/2001 | Yamazaki et al. .......... 424/85.1 |
| 6,525,102 | B1 | 2/2003 | Chen et al. .................. 514/970 |
| 6,548,020 | B2 | 4/2003 | Okamoto et al. ........... 422/68.1 |
| 6,569,406 | B2 | 5/2003 | Stevenson et al. ............. 424/43 |
| 6,627,187 | B2 | 9/2003 | Yamazaki et al. .......... 424/85.1 |
| 6,838,975 | B2 | 1/2005 | Litwiller et al. ............ 340/5.67 |
| 6,921,433 | B2 | 7/2005 | Kuribayashi et al. ........ 106/499 |

(Continued)

FOREIGN PATENT DOCUMENTS

EP    1 314 437 A1    5/2003

(Continued)

OTHER PUBLICATIONS

Allain et al., "Microarray sampling-platform fabrication using bubble-jet technology for a biochip system," Fresenius J. Anal. Chem., vol. 371, 2001, pp. 146-150.

(Continued)

*Primary Examiner*—Steven O Douglas
(74) *Attorney, Agent, or Firm*—Fitzpatrick, Cella, Harper & Scinto

(57) ABSTRACT

There is provided an ejection liquid which can be ejected stably by an inkjet method even in the case of containing at least one of proteins and peptides and is provided a method and device of discharging a liquid containing at least one of proteins and peptides, which use the ejection liquid. The ejection liquid to be ejected from ejection orifice by an inkjet method contains at least one selected from proteins and peptides, a benzalkonium chloride and a liquid medium.

4 Claims, 6 Drawing Sheets

U.S. PATENT DOCUMENTS

| | | | |
|---|---|---|---|
| 6,926,392 B2 | 8/2005 | Sasaki et al. | 347/65 |
| 6,964,700 B2 | 11/2005 | Uji et al. | 106/31.28 |
| 7,011,825 B2 | 3/2006 | Yamazaki et al. | 424/85.1 |
| 7,030,086 B2 | 4/2006 | Chen et al. | 514/12 |
| 7,083,667 B2 | 8/2006 | Murai et al. | 106/31.43 |
| 7,202,065 B2 | 4/2007 | Römisch et al. | 435/183 |
| 2002/0092519 A1 | 7/2002 | Davis | 128/200.14 |
| 2002/0110552 A1 | 8/2002 | Römisch et al. | 424/94.63 |
| 2002/0177221 A1 | 11/2002 | Nishiguchi et al. | 435/287.2 |
| 2003/0119179 A1 | 6/2003 | Okamoto et al. | 435/287.2 |
| 2003/0190316 A1 | 10/2003 | Kakuta et al. | 424/132.1 |
| 2004/0037803 A1 | 2/2004 | Sato | 424/85.1 |
| 2004/0045546 A1* | 3/2004 | Hirsh et al. | 128/200.14 |
| 2004/0259083 A1 | 12/2004 | Oshima | 435/6 |
| 2005/0188894 A1 | 9/2005 | Yamagishi et al. | 106/31.43 |
| 2006/0093576 A1 | 5/2006 | Chen et al. | 424/85.2 |
| 2006/0093598 A1 | 5/2006 | Chen et al. | 424/94.2 |
| 2006/0183046 A1 | 8/2006 | Murai et al. | 430/108.2 |
| 2007/0206081 A1 | 9/2007 | Masada et al. | 347/100 |
| 2007/0221215 A1 | 9/2007 | Sugita et al. | 128/203.12 |
| 2007/0277701 A1 | 12/2007 | Toyoda et al. | 106/31.48 |

FOREIGN PATENT DOCUMENTS

| | | |
|---|---|---|
| JP | 7-173073 A | 7/1995 |
| JP | 2002-148259 A | 5/2002 |
| JP | 2002-248171 | 9/2002 |
| JP | 2002-249441 A | 9/2002 |
| JP | 2002-355025 | 12/2002 |
| JP | 2003/510368 A | 3/2003 |
| JP | 2003-154655 | 5/2003 |
| JP | 2003/154665 A | 5/2003 |
| JP | 2004-515467 | 5/2004 |
| JP | 2004-196824 A | 7/2004 |
| JP | 2004-532861 A | 10/2004 |
| JP | 3610231 | 1/2005 |
| JP | 3618633 | 2/2005 |
| WO | WO 01/24814 A1 | 4/2001 |
| WO | WO 02/11695 A2 | 2/2002 |
| WO | WO 02/13860 A1 | 2/2002 |
| WO | WO 02/17957 A1 | 3/2002 |
| WO | WO 02/092813 A1 | 11/2002 |
| WO | WO 02/094342 A2 | 11/2002 |

OTHER PUBLICATIONS

Howard et al., "Ink-Jet Printer Heads for Ultra-Small-Drop Protein Crystallography," BioTechniques, vol. 33, No. 6, Dec. 2002, pp. 1302-1306.

Critical Reviews in Therapeutic Drug Carrier Systems, 12 (2 & 3) (1995), pp. 233-261.

Mar. 26, 2008 Japanese Official Action in Japanese Patent Appln. No. 2005-252154 (with translation).

Motonori Kudo, et al., "Control of Suppression/Promotion of Aggregation by Addition of Small Molecule", Summary Collection of Japan Society for Bioscience, Biotechnology and Agrochemistry Convention, 2002, vol. 2002, 216.

Kentaro Shiraki, "Small Molecule Additive for Suppressing Deactivation and Agglomeration of Protein", Biophysics, 2004, vol. 44, No. 2, pp. 87-90.

* cited by examiner

EJECTION LIQUID AND EJECTION METHOD

This is a continuation-in-part application of U.S. patent application Ser. No. 11/570,744 filed on Dec. 15, 2006, which is the National Stage of International Application No. PCT/JP2005/018247, filed on Sep. 27, 2005.

BACKGROUND OF THE INVENTION

1. Field of the Invention

The present invention relates to: a liquid composition suitable for making droplets from a liquid containing at least one of proteins and peptides and a method of ejecting such droplets.

2. Description of the Related Art

Currently, many attempts have been conducted to utilize a protein solution as liquid droplets. For example, for the drug delivery method, the liquid droplets have been considered to be applied in transmucosal administration because of, for example, advantages in that only a small amount of protein may be required in the production of a biochip or biosensor and the protein may be integrated easily. In addition, attentions have been paid on a method of using a fine liquid droplet of protein for control on crystallization of protein and also for screening of a physiologically active substance (see, for example, Japanese Patent Application Laid-Open No. 2002-355025, Allain L R et al., "Fresenius J. Anal. Chem", vol. 371, p. 146-150, 2001, and Howard E I and Cachau R E, "Biotechniques", vol. 33, p. 1302-1306, 2002).

In recent years, mass production of proteins, particularly useful proteins such as enzymes and those having physiological activities has become possible by any technology such as genetic recombinant technology. Therefore, the process of making protein into liquid droplets can be effective means in the field of searching, utilizing, and applying a novel protein medicine. More specifically, there are increasing significant demands on means for providing patients with many pharmaceutical agents by microdroplets. In particular, microdroplets have become important for the administration of proteins, peptides, and other biological materials from the lungs. In other words, the lung administration have been remarked as an administration route in place of an injection of a macromolecule peptide-based drug represented by insulin because the lungs have lung alveolis with their own extensive surface areas of 50 to 140 $m^2$ and the epithelium provided as a barrier of absorption is as thin as 0.1 μm, while the enzyme activities of the lungs are smaller than those of the gastrointestinal tract.

In general, the deposition of microdroplets of drug in the lungs has been known to depend largely on the mass median aerodynamic diameters thereof. In particular, the delivery of the microdroplets to the lung alveolis in the deep portions of the lungs essentially requires the administration of the droplets with high reproducibility which present between 1-5 μm of particle size and have a narrow particle size distribution.

As a method of preparing uniform droplets with a narrow particle size distribution, the use of a suitable droplet generator diverted from those used in inkjet printing in the production of extremely fine droplets and the application of the droplets have been reported in the art (see, for example, U.S. Pat. No. 5,894,841 and Japanese Patent Application Laid-Open No. 2002-248171). Here, the specific inkjet printing method concerned involves leading liquid to be ejected into a small chamber where the liquid is subjected to physical power, thereby allowing droplets of the liquid to be ejected from orifices. A discharging method may be any one of those known in the art, such as one that generates air bubbles spouting droplets through orifices formed on a chamber by means of electrical and thermal transducers such as thin-film resistors (i.e., a thermal inkjet method) and one that ejects liquid directly from orifices formed on a chamber by means of piezoelectric transducers (i.e., a piezo inkjet method).

For allowing the lungs to absorb a drug, the dose of the drug should be controlled. Therefore, making droplets from the liquid by the inkjet method, which is capable of adjusting the ejection amount thereof, is a very preferable configuration. On the other hand, however, the ejection of a solution should be surely carried out in this case. However, the ejection of a protein solution is unstable when the protein solution is only controlled with respect to its surface tension and coefficient of viscosity. Therefore, the difficulty in quantitative ejection has often occurred.

Problems associated with the process of making droplets of a protein or peptide using the inkjet method are due to the fact that the tertiary structure of the protein is brittle. Thus, the aggregation or degradation of the protein may occur when the configuration thereof is destroyed. When the process of making droplets is carried out using the inkjet method, the structures of many proteins may become unstable owing to physical stress such as pressure or shearing stress or to high surface energy peculiar to microdroplets (if the thermal inkjet method is employed, heat is further applied in addition to the above stress). In particular, in the case of the inkjet method, those physical actions are extremely larger than the shearing force and thermal energy to be applied by conventional stirring or heat treatment (for example, in the case of the thermal inkjet method, approximately 300° C. and 90 atm are applied momentarily). Furthermore, several physical stresses are impressed at the same time, so that the stability of protein may tend to be substantially lowered, compared with the case of usually handling the protein. On this account, the conventional technology for stabilizing protein may be insufficient when the inkjet technology is employed. If such a problem occurs, the protein may be aggregated at the time of making droplets and nozzles may be then clogged, thereby making it difficult to ejection droplets.

Furthermore, droplets having diameters of 1 to 5 μm, which are suitable for the lung administration, are extremely smaller than those having diameters of approximately 16 μm used in any printer commercially available at present. Therefore, a larger surface energy or shearing stress may be impressed on the droplets than on the droplets used in the printer. Therefore, it is more difficult to eject microdroplets suitable for inhaling protein into the lungs.

Meanwhile, a method in which a surfactant (surface-active agent), a water-soluble high polymer such as glycerol, a saccharide of various types or polyethylene glycol, and albumin or the like, are added is known as a method by which proteins and peptides are stabilized. However, in may cases, this method is little effective, or not effective at all, in improving the stability of ejection when proteins and peptides are ejected by the thermal inkjet method.

In the pamphlet of International Publication No. WO 02/094342, there is disclosed a compound for regulating surface tension and a method of adding a humectant for a liquid composition for the pulmonary absorption of a droplet prepared using a thermal inkjet method. Here, for increasing the stability of protein in a solution provided as droplets by the surface tension, viscosity, or moisturizing action of the solution, a surfactant or a water-soluble polymer such as polyethylene glycol is added.

However, there is no description about the stability of discharging, and also the addition of a surfactant or a water-soluble polymer exerts insufficient effects when the concentration of protein or peptide increases. In addition, there are more surfactants which have been recognized as of no effect at all than those having effects. Besides, the stability is defined by not only the surface tension and viscosity. Therefore, the method disclosed in the document is not a common practice for the stabilization of ejection. Therefore, for actual use, any liquid to be used for an ejection purpose, which is capable of discharging protein or peptide in a stable manner, becomes essential.

SUMMARY OF THE INVENTION

The present invention aims to provide: an ejection liquid to be provided for stably discharging droplets containing at least one of proteins and peptides by means of an inkjet method on the basis of the principle of the inkjet method; and an ejection method, a liquid-ejecting cartridge and an ejection device which are suitable for the ejection of the ejection liquid.

The ejection liquid of the present invention is an ejection liquid to be ejected from an orifice using inkjet method, containing: at least one selected from proteins and peptides; a benzalkonium chloride; and a liquid medium.

The ejection method of the present invention is characterized by ejecting the above ejection liquid on the principle of the inkjet method.

The liquid-ejecting cartridge of the present invention is characterized by having a tank in which the above ejection liquid is held, and an ejection head which has an electricity-heat conversion element capable of providing the ejection liquid with heat energy.

The ejection device of the present invention is characterized by having the liquid-ejecting cartridge constructed as described above, a flow path through which a liquid ejected from a liquid-ejecting part of an ejection head the cartridge has is guided to an inhalation portion of a user, and an opening.

According to the present invention, benzalkonium chloride is added to the solution containing at least one of proteins and peptides, so that an ejection liquid capable of being ejected stably in accordance with inkjet method.

Further features of the present invention will become apparent from the following description of exemplary embodiments with reference to the attached drawings.

DESCRIPTION OF THE EMBODIMENTS

Figure 1:
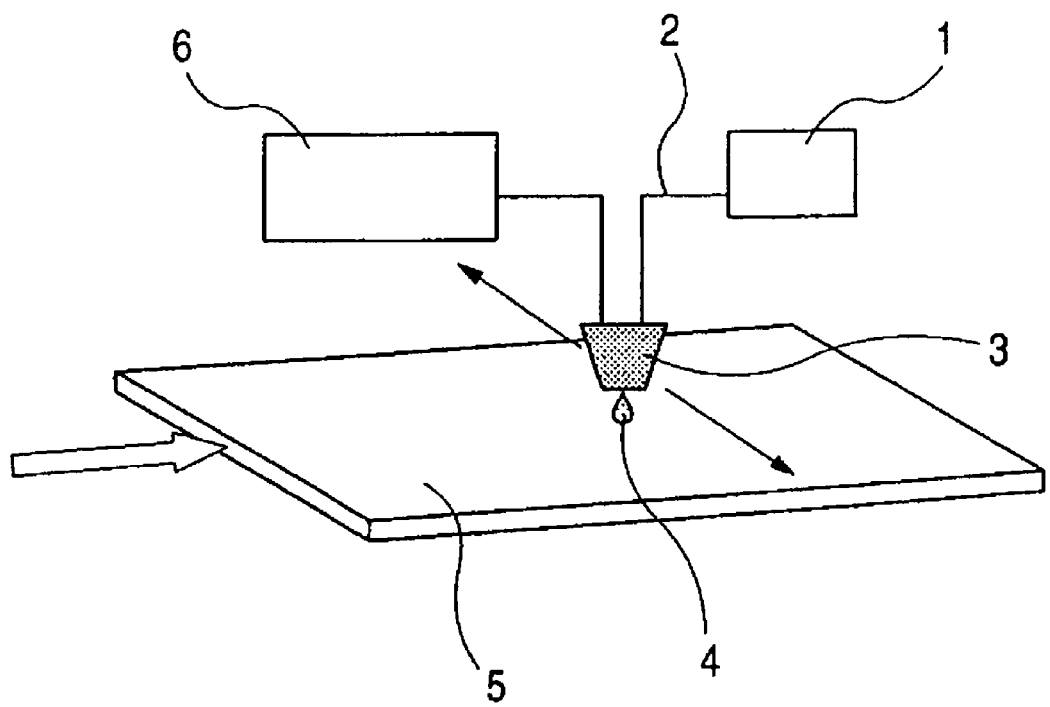
FIG. 1 is a schematic diagram for illustrating a method of discharging a solution containing a protein or peptide on a substrate.

The term "protein(s)" as used in the present invention refers to any polypeptide in which a number of amino acids are linked with each other by peptide linkages and which is dissolved or dispersed in an aqueous solution. In addition, the term "peptide(s)" as used in the present invention refers to a peptide in which two or more and 100 or less amino acids are being linked with each other by peptide linkages. Those proteins and peptides may be chemically synthesized or may be purified from those naturally occurred. Typically, they may be recombinants of native proteins and peptides. In general, the proteins and peptides can be chemically modified by covalently bonding amino acid residues to protein and peptide molecules, so that their therapeutic effects may be prolonged to attain improvements in their effects.

When the present invention is implemented, various kinds of proteins and peptides which are desired to be provided as droplets can be used. The proteins and peptides which can be used in the present invention are not specifically limited as far as they have physiological activities on the living bodies and retain their activities in the living bodies. Most typically, making the droplets from the proteins and peptides of the present invention is for the delivery of proteins and peptides which are useful for therapeutics to the lungs.

Examples thereof include: calcitonins; cyclosporine; blood coagulation factors; various hemopoietic factors such as G-CSF, GM-CSF, SCF, EPO, GM-MSF, and CSF-1; interleukins such as IL-1, IL-2, IL-3, IL-4, IL-5, IL-6, IL-7, IL-8, IL-9, IL-10, IL-11, and IL-12; IGFs; and cytokines such as M-CSF, thymosin, TNF, and LIF. Proteins having other useful therapeutic effects include vasoactive peptides, interferons (alpha, beta, gamma, and common interferon), growth factors and hormones such as human growth hormones and other animal growth hormones such as bovine, hog, and avian growth hormones, insulin, oxytocin, angiotensin, methionine-enkephalin, substance P, ET-1, FGF, KGF, EGF, IGF, PDGF, LHRH, GHRH, FSH, DDAVP, PTH, vasopression, glucagon, and somatostatin. Protease inhibitors may be also used, including leupeptin, pepstatin, and metalloproteinase inhibitors such as TIMP-1 and TIMP-2. Nerve growth factors such as BDNF and NT3 may be also used. In addition, plasminogen activators such as tPA, urokinase, and streptokinase may be also used. Any peptide moiety, which contains all or part of the main structure of a parent protein and retains at least a part of biological characteristics of the parent protein, may be also used. Any of the above substances modified with analogs, such as substituted or defective analogs, modified amino acids such as peptide analogs, and water-soluble polymers such as PEG and PVA may be also used. Critical Reviews in Therapeutic Drug Carrier Systems, 12 (2 & 3) (1995) clearly describes that the above mentioned proteins can be delivered to lung.

Furthermore, for the production of a biochip or biosensor and the use for screening proteins and peptides, in addition to the above proteins and peptides, the above substances modified with any of various enzymes such as oxidase, reductase, transferase, hydrase, lyase, isomerase, synthetase, epimerase, mutase, and rasease, various antibodies such as IgG and IgE, and antigens thereof, and proteins and peptides for diagnostic use, such as allergen, chaperonin, avidin, and biotin, and immobilizing agents may be also used.

Any protein or peptide in the ejection liquid may be one having a molecular weight ranging from 0.5 k to 150 kDa. The content of at least one selected from proteins and peptides, which is selected depending on purposes, ranges preferably from 1 μg/ml to 200 mg/ml, more preferably from 0.1 mg/ml to 60 mg/ml.

In general, it is known that the ejection of ink by the inkjet method may be improved by the addition of a surfactant or a solvent such as polyethylene glycol. However, the inventors have found that when the protein or peptide solution is ejected, an improvement in ejection ability cannot be recognized only by the addition and an additional additive may be required.

In the following description, the present invention will be described mainly with respect to a configuration using the thermal inkjet method because the thermal inkjet method shows the most significant improvement in ejection ability. In the present invention, piezoelectric inkjet method can be used, and an ejection method can be selected according to the kinds of protein and peptide to be ejected. In the present invention, among an inkjet method as usually used in a printing field, an embodiment capable of providing a thermal energy by using an electrothermal transducer is described as "thermal inkjet method" and an embodiment capable of providing a mechanical energy by using an electrothermal transducer is described as "piezo inkjet method". These terms are employed for a liquid containing proteins, but such terms are merely expressed providing a liquid with ejection energy according to the principle of the inkjet method.

As a result of extensive studies made by the present inventors, they have discovered that a solution prepared by adding a benzalkonium chloride to a solution containing at least one of proteins and peptides as effective components is suitable to be made into stable droplets on the principle of the inkjet method. The benzalkonium chloride used in the present invention corresponds to a case in which, in the benzalkonium represented by the following formula (1), $X_1$ is a chloride ion.

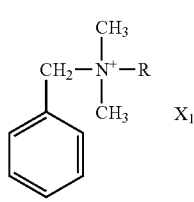

Formula (1)

R = $C_8H_{17}$ to $C_{18}H_{37}$

R in the formula (1) is a substituted or unsubstituted alkyl group having 8 to 18 carbon atoms, and may preferably be a saturated alkyl group having 8 to 16 carbon atoms. $X_1$ in the formula (1) is a counter ion, which may be of anionic species, and is at least one selected from an inorganic anion and an organic anion. As examples thereof, it may include halide ions such as chloride ions, bromide ions and iodide ions, hydroxide ions, carboxylate ions, nitrate ions, phosphate ions and sulfate ions. The counter ion may be of one kind or of two or more kinds.

The reason why the benzalkonium chloride contributes greatly to the stability of ejection is considered as stated below. The benzalkonium has a quaternary ammonium cation in the molecule, and also coexists with the counter anion to have hydration properties. It has also a feature that its hydration properties and ability to dissolve in water are so high that it can have high hydration properties even where it has a long-chain alkyl group in the molecule. On the other hand, the proteins and peptides are so strongly hydrophobic as to make it difficult to become stably hydrated. Inasmuch as the benzalkonium chloride has in its molecule the long-chain alkyl group, i.e., a hydrophobic group, the hydrophobic group acts on the hydrophobic moieties in the proteins and peptides, and also makes the proteins and peptides stably hydrated in virtue of hydration power of the cation and anion having high hydration properties. As the result, the mutual action of the proteins and peptides can be restrained. This action can keep the proteins and peptides from changing in properties and agglomerating because of energy loading coming when ejected on the principle of the thermal inkjet method, and also can stabilize the ejection.

The addition concentration of benzalkonium chloride is preferably 0.01 to 20% by weight, more preferably 0.1 to 10% by weight, although it depends on the type and concentration of protein or peptide.

In the present invention, it is found that the stable ejection can be retained by co-addition of benzalkonium chloride and the surfactant even if the concentrations of the additives are substantially reduced. The addition amount of benzalkonium chloride can be one-half to one-tenth of a solution having the same protein concentration by the addition of 0.2 to 1 part by weight of the surfactant with respect to one part by weight of benzalkonium chloride.

The effects of the surfactant are different from those of benzalkonium chloride and may include the action of preventing a protein from being denatured and the action of redissolving the aggregated protein to stabilize the ejection. A combination of those two different effects may lead to a synergistic effect to substantially improve the stability of ejection. The stability of ejection may not be secured because the surfactant cannot solely prevent the aggregation of protein completely because of poor levels of those actions.

The term "surfactant" as used in the present invention refers to a compound having both a polar moiety and a non-polar moiety in one molecule and also having a characteristic feature in that the moieties are on their respective different local areas on the molecule, the surfactant reduces two surface tensions in immiscible correlation by means of a molecular arrangement on the interface, and a micell can be formed.

Specifically, typical examples of the surfactant to be used, but not limited to, include: a sorbitan fatty acid ester such as sorbitan monocaprylate, sorbitan monolaurate, or sorbitan monopalmitate; an N-acylamino acid of a surfactant having an amino acid as a hydrophilic group such as N-coconut oil fatty acid glycine, N-coconut oil fatty glutamic acid, or N-lauroyl glutamic acid; a fatty acid salt of amino acid; a glycerin fatty acid ester such as glycerin monocaprylate, glycerin monomyristate, or glycerin monostearate; a polyglycerin fatty acid ester such as decaglyceryl monostearate, decaglyceryl distearate, or decaglyceryl monolinolate; a polyoxyethylene sorbitan fatty acid ester such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, or polyoxyethylene sorbitan tristearate; a polyoxyethylene sorbitol fatty acid ester such as polyoxyethylene sorbitol tetrastearate or polyoxyethylene sorbitol tetraoleate; a polyoxyethylene glycerin fatty acid ester such as polyoxyethylene glyceryl monostearate; a polyethylene glycol fatty acid ester such as polyethylene glycol distearate; a polyoxyethylene alkyl ether such as polyoxyethylene lauryl ether; a polyoxyethylene polyoxypropylene alkyl ether such as polyoxyethylene polyoxypropylene glycol ether, polyoxyethylene polyoxypropylene propyl ether, or polyoxyethylene polyoxypropylene cetyl ether; a polyoxyethylene alkylphenyl ether such as polyoxyethylene nonylphenyl ether; a polyoxyethylene hardened castor oil such as polyoxyethylene castor oil, polyoxyethylene hardened castor oil (polyoxyethylene hydrogenated castor oil); a polyoxyethylene beeswax derivative such as polyoxyethylene sorbitol beeswax; a polyoxyethylene lanolin derivative such as polyoxyethylene lanolin; a surfactant having HLB 6 to 18 such as a polyoxyethylene fatty acid amide (for example, polyoxyethylene stearamide); an anionic surfactant such as an alkyl sulfate having 8 to 18 carbon atoms (for example, sodium cetyl sulfate, sodium lauryl sulfate, or sodium oleyl sulfate); a polyoxyethylene alkyl ether sulfate having the average number of additional moles of 2 to 4 of ethylene oxide and 8 to 18 carbon atoms at an alkyl group (for example, sodium polyoxyethylene lauryl sulfate); an alkyl benzene sulfonate having 8 to 18 carbon atoms at an alkyl group such as sodium lauryl benzene sulfonate; an alkyl sulfosuccinate having 8 to 18 carbon atoms at an alkyl group such as sodium lauryl sulfosuccinate; a natural surfactant such as lecithin or glycerophospholipid; a sphingophospholipid such as sphingomyelin; and a saccharose fatty acid ester of a fatty acid ester having 8 to 18 carbon atoms. Those surfactants were added, alone or in combination with two kinds or more, to an ejecting liquid (liquid compositions) of the present invention.

Preferable surfactants include polyoxyethylene sorbitan fatty acid ester, and particularly preferable surfactants include polyoxyethylene 20 sorbitan monolaurate, polyoxyethylene (4) sorbitanmonooleate, polyoxyethylene 20 sorbitan monopalmitate, polyoxyethylene 20 sorbitan monostearate, polyoxyethylene 20 sorbitan tristearate, polyoxyethylene (5) sorbitanmonooleate, and polyoxyethylene 20 sorbitantrioleate. Of those, most preferable surfactants include polyoxyethylene 20 sorbitan monolaurate, polyoxyethylene 20 sorbitan monooleate. In addition, those preferable for pulmonary inhalation include polyoxyethylene 20 sorbitan monolaurate and polyoxyethylene 20 sorbitan monooleate.

The liquid medium may preferably chiefly be composed of water from the viewpoint of dissolving properties of proteins and the like. The water in the medium may preferably be in a proportion of 50% or more. In addition to the water that is the main component of the medium, a mixed solvent may be used which contains a water-soluble organic solvent such as alcohol.

As specific example of the water-soluble organic solvent, it may include, e.g., amides such as dimethylformamide and dimethylacetamide; ketones such as acetone; ethers such as tetrahydrofuran and dioxane; alcohols such as ethanol; polyalkylene glycols such as polyethylene glycol and polypropylene glycol; alkylene glycols the alkylene group of which has 2 to 6 carbon atoms, such as ethylene glycol, propylene glycol, butylene glycol, triethylene glycol, 1,2,6-hexanetriol, thiodiglycol, hexylene glycol and diethylene glycol; glycerol; lower alkyl ethers of polyhydric alcohols, such as ethylene glycol monomethyl (or -ethyl)ether, diethylene glycol monomethyl (or -ethyl)ether and triethylene glycol monomethyl (or -ethyl)ether; and N-methyl-2-pyrrolidone.

In the present invention, the protein, the amino acid and the surfactant may previously be mixed, or may be mixed immediately before ejection. These may preferably uniformly be mixed before ejection.

In the embodiments of the present invention, for removing microbial effects, an antimicrobial agent, a germicidal agent, and an antiseptic agent may be added. Examples of those agents include: phenolic derivatives such as phenol, cresol, and anisole; quaternary ammonium salts such as benzalkonium chloride and benzatonium chloride; benzoic acids such as benzoic acid and paraoxybenzoic acid ester; and sorbic acid.

In some embodiments of the present invention, for elevating physical stability in conservation, any one of oil, glycerin, ethanol, urea, cellulose, polyethylene glycol, and alginate may be added. In addition, for elevating chemical stability, ascorbic acid, citric acid, cyclodextrin, tocopherol, or any other anti-oxidizing agent may be added.

Any buffer may be added to adjust the pH of the ejection liquid. Examples of the buffer, which may be used, include ascorbic acid, citric acid, diluted hydrochloric acid, and diluted sodium hydroxide, and also include other buffers such as sodium hydrogenphosphate, sodium dihydrogen phosphate, potassium hydrogenphosphate, potassium dihydrogen phosphate, PBS, HEPES, and Tris.

Aminoethylsulfonic acid, potassium chloride, sodium chloride, glycerin, or sodium bicarbonate may be added as an isotonizing agent.

Any one of saccharides such as glucose and sorbitol, sweetening agents such as aspartame, menthol, and various aromatics may be added as a flavoring agent. The lipophilic agents as well as lipopholic agents such as oily ones can be used.

Various additives adapted to the purpose for which the spray liquid to be applied is used may further optionally be added in proper quantities, as exemplified by a surface modifier, a viscosity modifier, a solvent and a humectant.

Stated specifically, as additives that may be mixed, they may be exemplified by a hydrophilic binder, a hydrophobic binder, a hydrophilic thickening agent, a hydrophobic thickening agent, glycol derivatives, alcohols, flavoring components and an electrolyte, any of which may be selected and may be used alone or in the form of a mixture(s).

In regard to various substances utilized as the additives exemplified above, it is preferable to use those used in medical purposes, listed in a pharmacopoeia or the like of every country as secondary components which can be added in preparing therapeutic solutions, or those which are admitted as being utilizable in food and cosmetics.

Various substances mixed as the additives may differ depending on their types and combination and also on the types of the proteins and peptides to which the substances are to be added. In general, from the viewpoint of ejection performance, they may each preferably be added in an amount selected within the range of from 0.01% weight to 40% by weight, and more preferably within the range of from 0.1% weight to 20% by weight.

When the above ejection liquid is used for the production of a biochip or biosensor or for screening of protein, a system, which is almost the same as an inkjet printer commercially available at present, can be used.

The ejection device (liquid-ejecting device) according to the present invention has an ejection head which can eject microdroplets of the liquid by the thermal inkjet method, and may preferably be so constructed that a large number of ejection units constituting the head may independently be driven. In such a case, the part of electrical connection that is used to connect a plurality of control signals required for such independent drive of the individual ejection units and the wiring for connection between the individual ejection units are set integral. In addition, it is preferable to set up a form of a liquid-ejecting cartridge in which a tank which holds the ejection liquid therein and an ejection head having an electricity-heat conversion element capable of providing the ejection liquid with heat energy are integrally constructed.

FIG. 1 schematically shows a device for performing the formation of protein spots on a substrate, making use of the ejection liquid according to the present invention. A substrate 5 is utilized as a detection plate where areas are formed in which reference materials such as proteins, peptides, enzymes and antibodies for detecting, e.g., various substances contained in a specimen are to be fixed. An ejection head 3 has at least i) liquid channels (not shown) where the liquid is provided with ejection energy and ii) ejection orifices (not shown) communicating the liquid channels. The liquid fed from a tank 1 holding the liquid therein to the liquid through a liquid-feeding path 2 is provided with heat energy, and the liquid is ejected as droplets 4 from the ejection orifices to the substrate 5 surface at its predetermined positions. The substrate 5 is disposed on a stage which can be positioned in the plane direction shown by an arrow. Thus, the position of impact of the droplets 4 on the substrate 5 is adjusted by moving the stage. The timing at which the droplets 4 are ejected is controlled by a drive controller 6 connected electrically to the ejection head 3.

Figure 2:
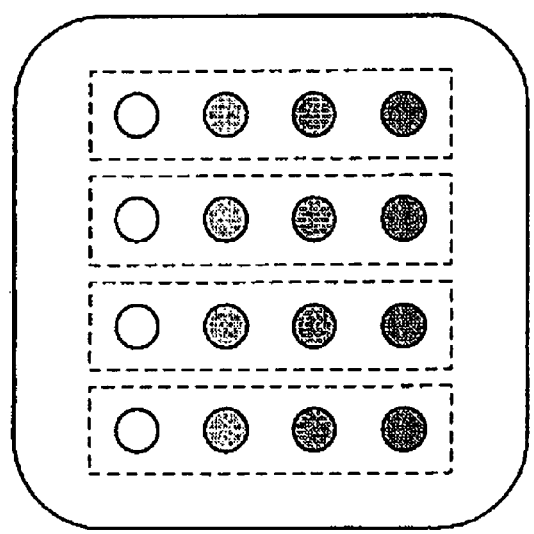
FIG. 2 is an illustration of one pattern for arranging a spot of protein on a surface of a substrate.

FIG. 2 shows as a plan view an example of protein spots arranged at the substrate surface. In FIG. 2, tones of the spots indicate the height of protein and peptide concentration. Areas surrounded by dotted lines are each spotted with one kind of ejection liquid. In the example shown in FIG. 2, a plurality of independently drivable ejection units from which ejection liquids different from one another are ejected may be disposed at the part of the ejection head. Feed systems for stated ejection liquids may be connected to the respective units to form two or more kinds of spots on the substrate. Further, the quantity in which the liquid is applied at each position of spot formation may be changed to form spots with liquids applied in different quantities.

As the ejection head 3, one constructed variously according to the size and arrangement density of the spots to be formed on the substrate may be utilized. Where the quantity of one droplet is set in the order of subpicolitter or femtolitter, it is preferable to use an ultramicrodroplet ejection head having superior droplet quantity controllability in such order, which is disclosed in Japanese Patent Application Laid-open No. 2003-154655.

A case in which the ejection liquid according to the present invention is used for spraying, in particular, a case in which it is used in an inhaler is described next. As the inhaler, it is preferable to use an inhaler constructed to independently have a part where the ejection liquid (a solution) is converted into fine droplets and a part where the liquid having been sprayed in microdroplets is mixed into air streams for transporting it. Thus, the part where the liquid is converted into fine droplets and the part where the air streams containing the microdroplets are formed are separated. This enables more uniform adjustment of ejection quantity. That is, the quantity of proteins and peptides as effective components, i.e., the quantity prescribed for each single-time administration can more uniformly be adjusted in the air streams when a person to be administered is made to inhale the air streams. The ejection head part may also be so constructed as to eject effective components which are different for each of the plurality of units having a large number of ejection orifices as described above. This enables control of ejection quantities of the plurality of effective components.

As the ejection head serving as a spray mechanism, an ejection head may be used which allows disposition of ejection orifices in a high density and is drivable on the principle of the thermal inkjet method. This enables easy miniaturization of inhalers portable by users.

In an inhaler for lung administration, it is important that the droplets contained in the air streams have a particle diameter of from 1 to 5 μm and also have a narrow particle size distribution. When also as portable one, it is further necessary for the inhaler to be of compact construction.

Figure 3:
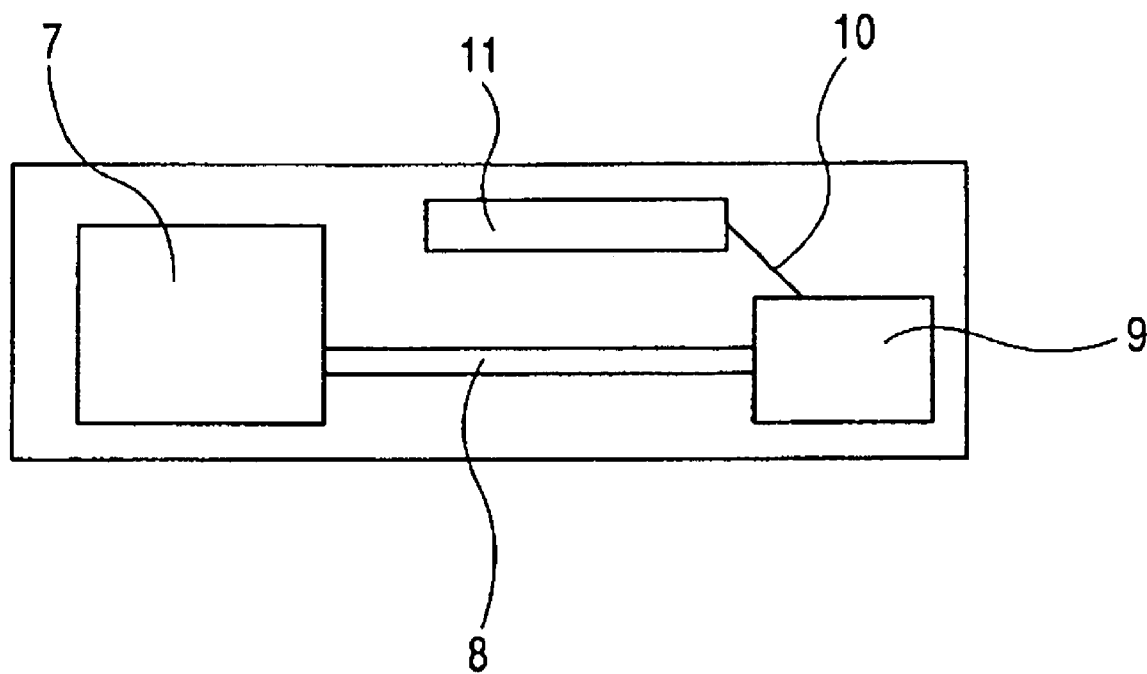
FIG. 3 is a schematic diagram for illustrating an inhalation head cartridge unit.

An example of a liquid-ejecting part such an inhaler has is schematically shown in FIG. 3. This liquid-ejecting part consists basically of a head 9, a tank 7 which holds the ejection liquid therein, a liquid flow path 8 through which the ejection liquid is fed from the tank 7 to the head 9, a controller 11 which controls the driving of the head 9 and a wiring 10 which connects the head 9 and the controller 11 electrically. This liquid-ejecting part further has structure as a head cartridge unit in which the above component parts are integrally formed. This head cartridge unit may optionally be so constructed as to be detachably mountable to the inhaler. As the head 9, what has construction of the droplet ejection head disclosed in Japanese Patent Application Laid-open No. 2003-154665 is preferred.

An example of a portable inhaler (inhaler) having the head cartridge unit constructed in this way is described with reference to FIGS. 4 and 5. The inhaler shown in FIGS. 4 and 5 has construction of an example in which it is made compact so that a user can carry it as an inhaler used for medical purposes.

Figure 4:
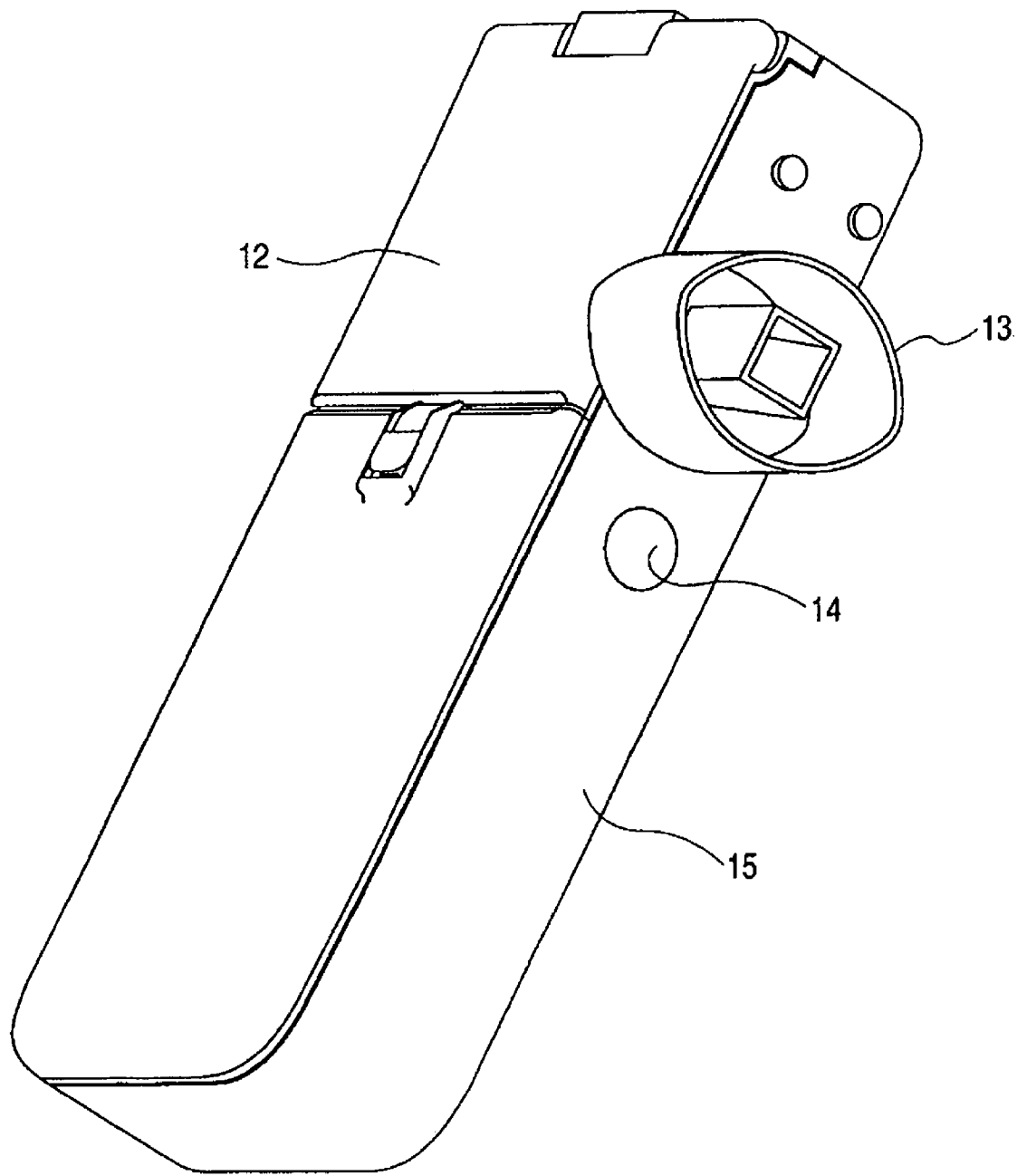
FIG. 4 is a perspective diagram of an inhaler.

FIG. 4 is a perspective diagram showing an external view of the inhaler, where reference numeral 15 denotes the body of the inhaler and 12 denotes an access cover, and the body and the cover form a housing. In FIG. 5, there is shown the access cover 12 being opened. When the access cover 12 is opened, a head cartridge unit 16 and a mouthpiece 13 can be seen. When a user performs an inhalation movement, the air can enter the mouthpiece 13 through an air intake and be then mixed with a drug ejected from an ejection orifice formed in the head part of the head cartridge unit 16, followed by moving toward the outlet of the mouthpiece in the form of allowing a person to sputter. The user puts the tip of the mouthpiece into the mouth and then holds it by teeth, followed by drawing in a breath. Thus, the drug solution ejected as droplets from the liquid ejection part of the head cartridge unit can be inhaled effectively.

Furthermore, the head cartridge unit 16 can be designed so as to be removably attached on the inhaler if necessary.

Figure 5:
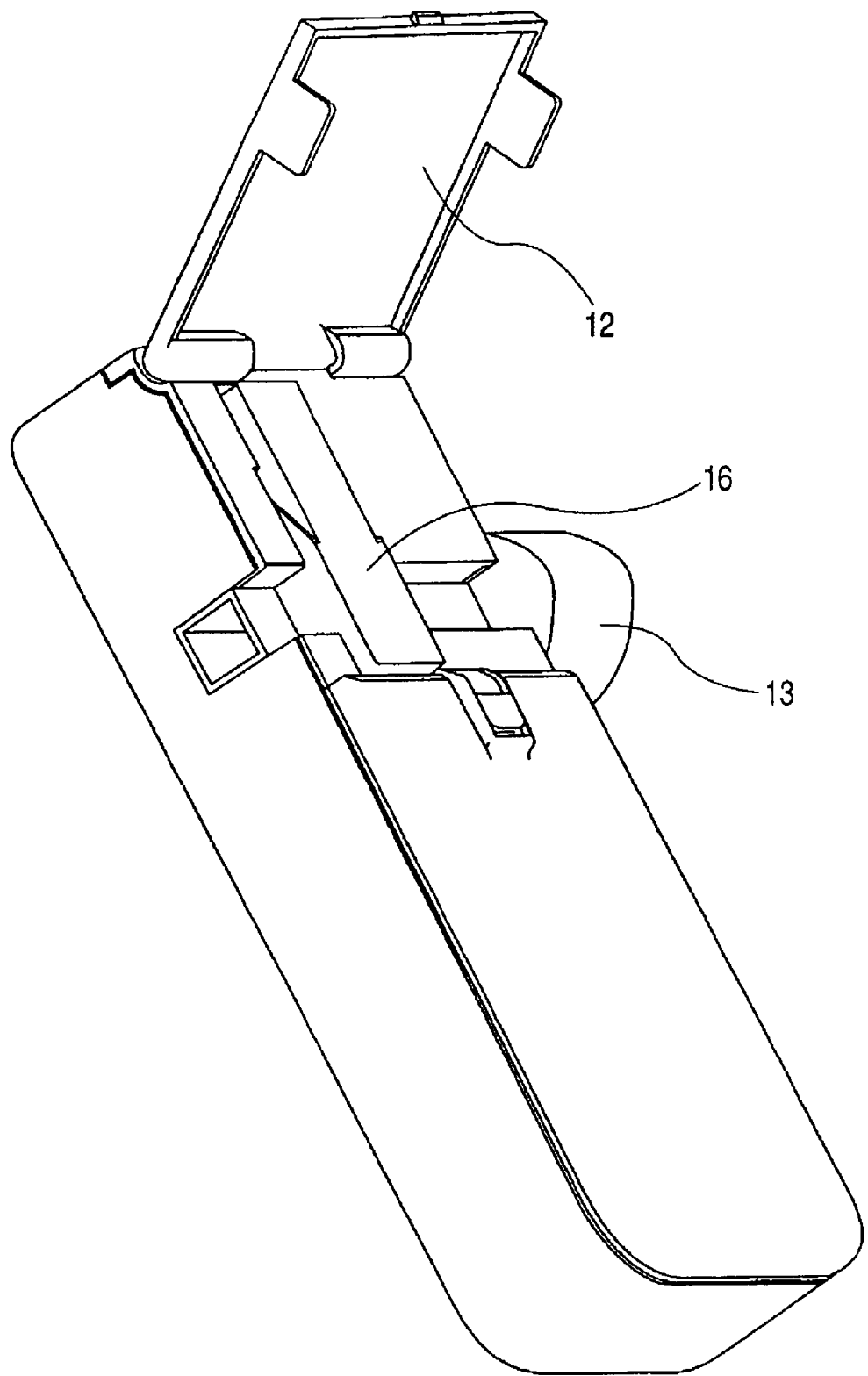
FIG. 5 is a perspective diagram of a state in which an access cover is opened in FIG. 4.

By adopting the configuration shown in FIGS. 4 and 5, microdroplets formed can naturally reach the throat, and the inside of the trachea, of the subject to which they are to be administered with inspired air. Therefore, the amount of the nebulized liquid (the dosage of active ingredient) can be independently controlled without depending on the volume of air to be inhaled.

EXAMPLES

Reference Example

Figure 6:
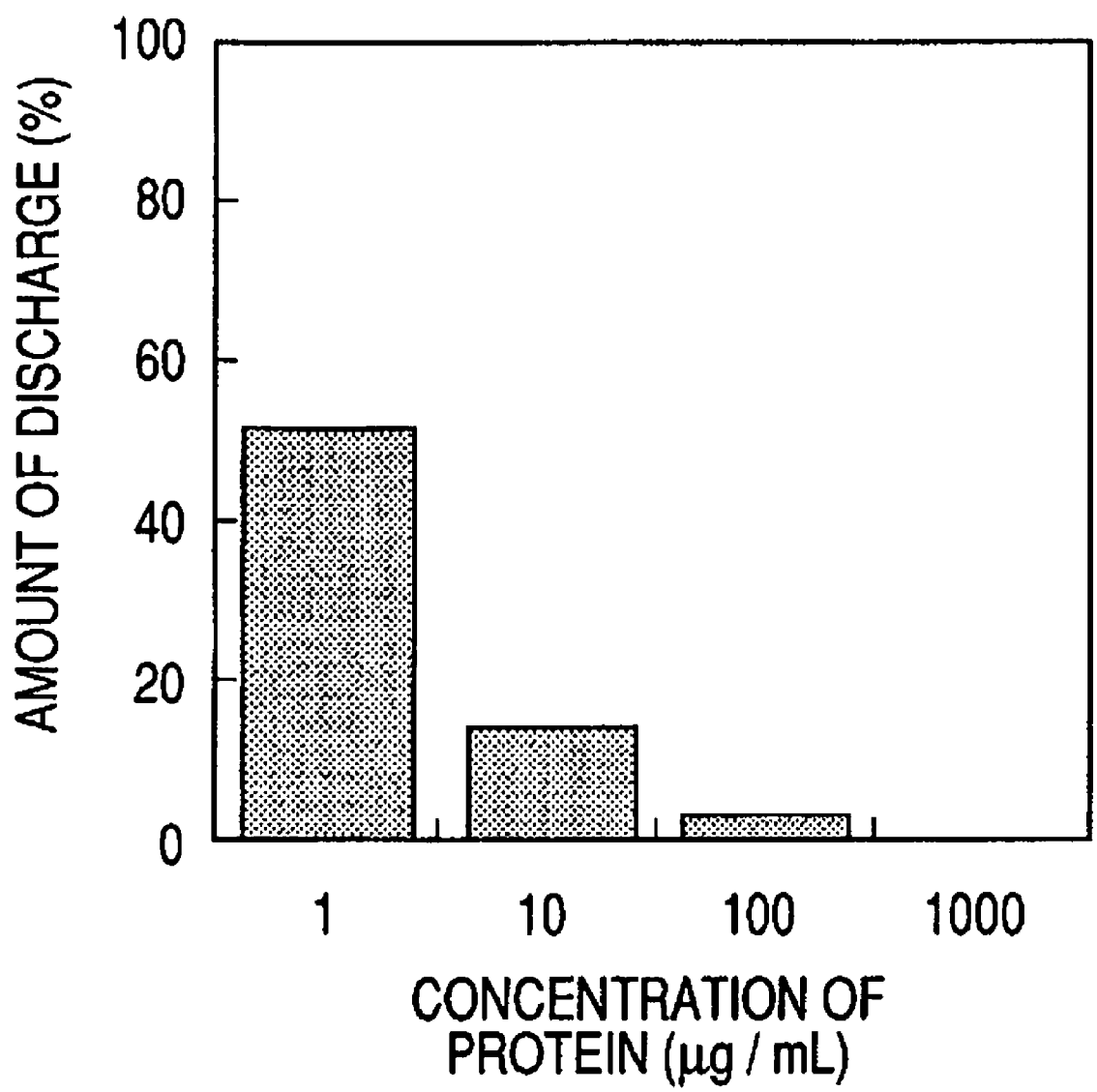
FIG. 6 is a graphical representation of the ejection amount of an albumin solution when it is ejected using a thermal inkjet method.

Before carrying out the example, for more understanding the difficulty in ejection of a protein solution, the ejection amounts are represented when only the protein is ejected by the thermal inkjet method. The protein solution used is albumin dissolved in phosphoric acid buffer and then ejected at each concentration using a thermal inkjet printer (trade name: PIXUS 950i, manufactured by Canon Inc.) which is a remodeled product for collecting the solution. In contrast, the ejection amounts of the respective albumin solutions are represented with respect to the amount of pure water similarly ejected, which is defined as 100%. The results are shown in FIG. 6.

The stability of ejection is not complete even when the concentration of albumin is as small as 1 μg/ml. The ejection becomes gradually more difficult as the concentration of the protein increases. In the inhaler, droplets to be ejected must have smaller sizes, so it may be difficult to eject a protein solution.

Hereinafter, the present invention will be described in more detail with reference to the examples. Here, "%" stands for "% by weight".

Examples 1 to 11 and Comparative Examples 1 to 15

Preparing Droplets of Protein Solution with Thermal Inkjet Method

The procedure of preparing an ejection liquid was carried out such that albumin was previously dissolved in purified water at an appropriate concentration and then stirred while benzalkonium chloride was added, followed by adjusting the concentrations of the respective substances to predetermined constant levels using purified water.

Previously, the head cartridge having a nozzle diameter of 3 μm to be used for an ejection experiment was filled with a 30% ethanol aqueous solution. Subsequently, a laser diffraction type measuring device for particle size distribution (SprayTec, manufactured by Malvern Co., Ltd.) was used for measuring particle size and particle size distribution to detect droplets having a particle size distribution sharply found at 3 μm.

The above head cartridge having a nozzle diameter of 3 μm was filled with an ejection liquid prepared in advance and then connected to an ejection controller, followed by carrying out ejection for 1 second at a frequency of 20 kHz at a voltage of 12V with an interval of 3 seconds to the subsequent ejection. This procedure was repeated 50 times, followed by visually observing whether the ejection occurred. The case where ejection occurred 50 times or more was evaluated as A, the case where ejection occurred 15 times or more but less than 50 times was evaluated as B, and the case where ejection occurred less than 15 times evaluated as C. In addition, HPLC assay was carried out on the ejection liquid before and after the ejection thereof (assay conditions: device; JASCO Corp., Column; YMC-Pack Diol-200,500×8.0 mm ID, Eluent; 0.1 M $KH_2PO_4$—$K_2HPO_4$ (pH 7.0) containing 0.2 M NaCL, Flow rate; 0.7 ml/min, Temperature; 25° C., Detection, UV at 215 nm) to observe a change in composition of the ejection liquid.

As comparative examples, ejection liquids were prepared using pure water, various protein solutions, and substances other than those used for the present invention and an experiment was then carried out such that the respective liquids were ejected by the same way as that of the examples. Here, the formulations studied for the examples and comparative examples and the results thereof were listed in Table 1 below.

TABLE 1

| | Protein | | Benzalkonium chloride | Surfactant and additive | | Ejection performance |
|---|---|---|---|---|---|---|
| | Type | Concentration | Concentration | type | Concentration | Evaluation |
| Example: | | | | | | |
| 1 | Albumin | 1 mg/ml | 40 mg/ml | None | — | A |
| 2 | Insulin | 4 mg/ml | 40 mg/ml | None | — | A |
| 3 | Glucagon | 0.5 mg/ml | 40 mg/ml | None | — | A |
| 4 | Human growth hormone | 1 mg/ml | 40 mg/ml | None | — | A |
| 5 | Interferon α | 1 mg/ml | 40 mg/ml | None | — | A |
| 6 | Interferon β | 1 mg/ml | 40 mg/ml | None | — | A |
| 7 | Interferon γ | 1 mg/ml | 40 mg/ml | None | — | A |
| 8 | Interleukin 2 | 1 mg/ml | 40 mg/ml | None | — | A |
| 9 | Carcitonin | 1 mg/ml | 40 mg/ml | None | — | A |
| 10 | GLP-1 | 1 mg/ml | 40 mg/ml | None | — | A |
| 11 | Erythropoietin | 1 mg/ml | 40 mg/ml | None | — | A |
| Comparative Example: | | | | | | |
| 1 | Water | — | — | — | — | A |
| 2 | Albumin | 1 mg/ml | None | None | — | C |
| 3 | Insulin | 4 mg/ml | None | None | — | C |
| 4 | Glucagon | 0.5 mg/ml | None | None | — | C |
| 5 | Human growth hormone | 1 mg/ml | None | None | — | C |
| 6 | Interferon α | 1 mg/ml | None | None | — | C |
| 7 | Interferon β | 1 mg/ml | None | None | — | C |
| 8 | Interferon γ | 1 mg/ml | None | None | — | C |
| 9 | Interleukin 2 | 1 mg/ml | None | None | — | C |
| 10 | Carcitonin | 1 mg/ml | None | None | — | C |
| 11 | GLP-1 | 1 mg/ml | None | None | — | C |
| 12 | Erythropoietin | 1 mg/ml | None | None | — | C |
| 13 | Albumin | 1 mg/ml | None | TWEEN80 | 10 mg/ml | C |
| 14 | Insulin | 4 mg/ml | None | TWEEN20 | 10 mg/ml | B |
| 15 | Insulin | 4 mg/ml | None | TWEEN20 | 50 mg/ml | C |

Pure water of Comparative Example 1 was ejected stably without a break because of no protein in the pure water. However, each of Comparative Examples which contained protein could not be ejected at all or was ejected little without depending on the kind of protein and the presence or absence of additives. When the surfactant Tween types was added as represented in Comparative Examples 13 to 15, the ejection occurred to some extent but resulted in poor stability. On the other hand, in each of Examples 1 to 11, the ejection was carried out normally and stabilized. As a result of HPLC analysis, in each of Examples 1 to 11, there were no changes in peak position and in peak area before and after the ejection and also no change was recognized in the liquid composition.

Examples 12 to 15

Synergistic Effect of Benzalkonium Chloride with Surfactant

Ejection liquids were prepared such that a surfactant was added to a solution added with benzalkonium chloride in protein. The resulting ejection liquids were evaluated by the same ejection experiment as that of Example 1. Here, formulations studied in the examples and the results obtained were listed in Table 2 below.

TABLE 2

| Example: | Protein | | Benzalkonium chloride | Surfactant and additive | | Ejection performance |
|---|---|---|---|---|---|---|
| | Type | Concentration | Concentration | type | Concentration | Evaluation |
| 12 | Insulin | 4 mg/ml | 10 mg/ml | TWEEN80 | 10 mg/ml | A |
| 13 | Insulin | 4 mg/ml | 10 mg/ml | TWEEN20 | 10 mg/ml | A |
| 14 | Insulin | 4 mg/ml | 10 mg/ml | Lauroyl-sarcosine | 5 mg/ml | A |
| 15 | Albumin | 1 mg/ml | 10 mg/ml | TWEEN20 | 5 mg/ml | A |

When benzalkonium chloride and surfactant were added at the same time, it was possible to eject the protein solution at an extremely smaller concentration than that of one added with benzalkonium chloride only. Besides, the amounts of the additives were largely decreased as a whole. As a result of carrying out HPLC assay on each of Examples 12 to 16, there was no change in peak chart before and after the ejection and no change was found in the liquid composition.

Example 16

Manufacture of Antibody Chip Using Inject Printer and Sensing

Figure 7:
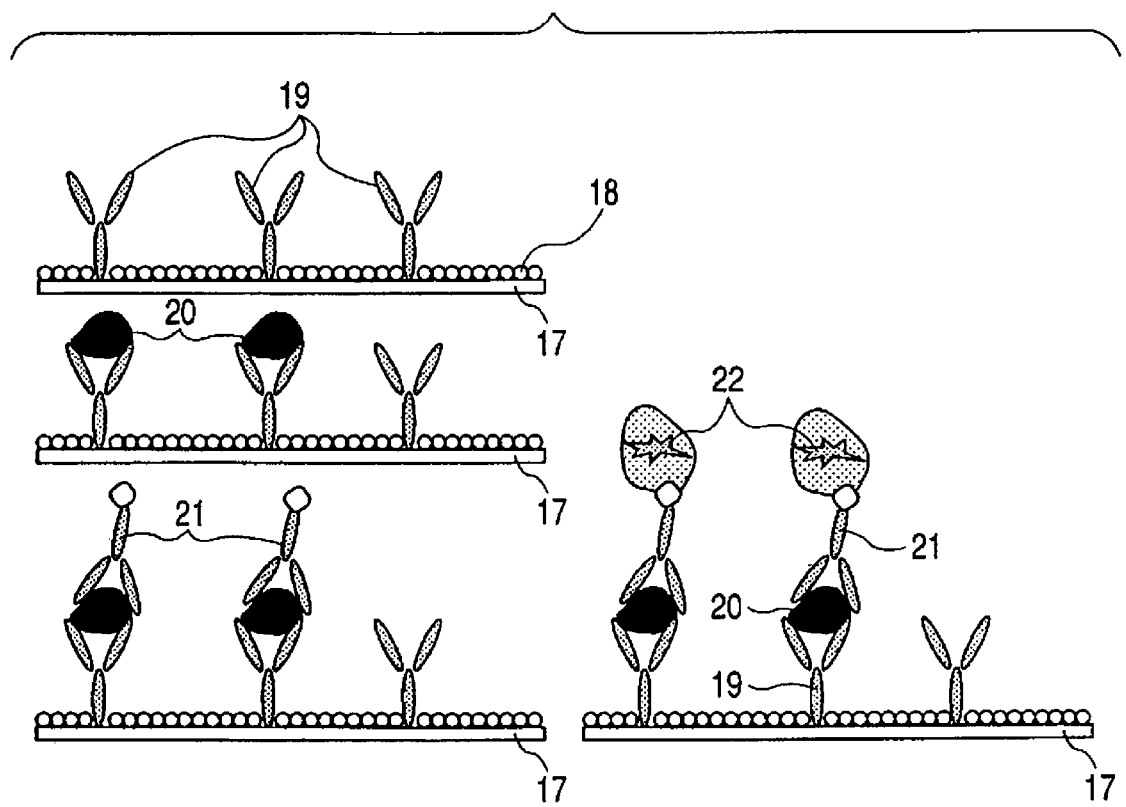
FIG. 7 is a diagram of a model of the experiment method of Example 16.

FIG. 7 shows a model of this example.

Each of human IL2 monoclonal antibody, human IL4 monoclonal antibody, and human IL6 monoclonal antibody was prepared at a concentration of 0.1 to 500 µg/ml. Here, benzalkonium chloride was added so as to become 5% (w/w) to prepare an ejection liquid. The resulting solution was filled in a head of an inkjet printer (trade name: PIXUS 950i, manufactured by Canon Inc.) and then ejected on a poly-L-Lysine-coated slide glass to form antibody spots in prescribed arrangement pattern. Reference numeral 19 shows each of the above antibodies as a substance specifically reacted with the substance to be detected.

The glass after ejection was incubated at 4° C., and the incubated glass was then masked with 1% BSA. Reference numeral 18 denotes BSA as a masking agent. After masking, the glass was washed very well and then provided as an antibody-chip substrate.

The chip and test substances, recombinants IL2, IL4, and IL6 as a substance 20 to be detected, each 1 µg/ml, were prepared together with 3.0% benzalkonium chloride (w/w), 0.5% Tween 20 (w/w), and 0.1% BSA (w/w), respectively. The solution was filled in the head of the inkjet printer (trade name: PIXUS 950i, manufactured by Canon Inc.) and then ejected on the above substrate with the same patterns. After discharging, a cover glass was placed on the substrate and allowed to react at 4° C. After the reaction, the antibody-chip was washed very well and then dried, and was used as substrate for detection.

Subsequently, the substrate was subjected to a reaction with a substance 21 which could be specifically attached to the sample, and the substance was then labeled. Each of antibody solutions which were labeled with biotin as substances 21 specifically attached to the sample (biotinylated human IL2 monoclonal antibody, biotinylated human IL4 monoclonal antibody, and biotinylated human IL6 monoclonal antibody) was prepared so as to become a final concentration of 1 µg/ml together with 3.0% benzalkonium chloride (w/w), 0.5% Tween 20 (w/w), and 0.1% BSA (w/w), followed by being filled in the head of the inkjet printer (trade name: PIXUS 950i, manufactured by Canon Inc.) and then ejected on the above substrate with the same patterns. After discharging, a cover glass was placed on the substrate and allowed to react at 4° C. After the reaction, the resultant was washed very well and then dried.

For labeling, 10 µg/ml of Cy3-labeled streptavidine 22 was prepared so as to become a final concentration of 3.0% benzalkonium chloride (w/w), 0.5% Tween 20 (w/w), and 0.1% BSA (w/w), followed by being filled in the head of the inkjet printer (trade name: PIXUS 950i, manufactured by Canon Inc.) and then ejected on the above substrate with the same patterns. After discharging, a cover glass was placed on the substrate and allowed to react at 4° C. After the reaction, the resultant was washed very well and then dried.

After that, excitation light was applied to the post-reaction substrate and the level of a fluorescence signal was then measured with respect to the emission of Cy3 using a fluorescence scanner on which a filter having a transmission wavelength of 532 nm had been placed. Consequently, fluorescence signals depending on the types and concentrations of the samples were detected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims priority from Japanese Patent Application Nos. 2004-279864 filed Sep. 27, 2004, 2005-252154 filed Aug. 31, 2005 and 2006-085565 filed Mar. 27, 2006, which are hereby incorporated by reference herein.

What is claimed is:

1. A liquid-ejection method employing a liquid-ejection device comprising a liquid-ejection head for ejecting a liquid by a thermal inkjet system, a tank for holding a liquid, and a liquid-feeding path for supplying the liquid held in the tank to the liquid-ejection head, the method comprising:

a step of ejecting the liquid from the liquid-ejection head by (i) supplying the liquid held in the tank to the liquid-ejection head through the liquid-feeding path, and (ii) applying an ejection energy to the liquid supplied, wherein the liquid comprises (i) at least one selected from proteins and peptides, (ii) a benzalkonium chloride, and (iii) a liquid medium containing water as a main component.

2. The liquid-ejection method according to claim 1, wherein at least one of the proteins and peptides is at least one of substances selected from carcitonins, insulins, glucagons, interferons, protease inhibitors, cytokines, growth hormones, hematopoietic factor proteins, and antibodies; and analogues of any of these, and derivatives of any of these.

3. The liquid-ejection method according to claim 1, further comprising a surfactant other than benzalkonium chloride.

4. The liquid-ejection method according to claim 3, wherein the surfactant comprises polyoxyethylene sorbitan fatty acid ester.

* * * * *